US00PP35749P2

(12) United States Plant Patent
Robb

(10) Patent No.: US PP35,749 P2
(45) Date of Patent: Apr. 16, 2024

(54) ***MAGNOLIA* PLANT NAMED 'SL01'**

(50) Latin Name: ***Magnolia laevifolia* x *figo***
Varietal Denomination: SL01

(71) Applicant: Paradise Seed Company Limited, Kulnura (AU)

(72) Inventor: John B. Robb, Kariong (AU)

(73) Assignee: Paradise Seed Company Limited, Kulnura (AU)

( * ) Notice: Subject to any disclaimer, the term of this patent is extended or adjusted under 35 U.S.C. 154(b) by 0 days.

(21) Appl. No.: 18/185,368

(22) Filed: Mar. 17, 2023

(51) Int. Cl.
*A01H 5/02* (2018.01)
*A01H 6/00* (2018.01)

(52) U.S. Cl.
USPC ..... Plt./223

(58) Field of Classification Search
USPC ..... Plt./223
CPC ..... A01H 5/02; A01H 5/00; A01H 6/00
See application file for complete search history.

(56) References Cited

PUBLICATIONS

NC State Extension for *Magnolia figo*, retrieved on Jul. 12, 2023 at https://plants.ces.ncsu.edu/plants/magnolia-figo/, 4 pp. (Year: 2023).*
NC State Extension for *Magnolia laevifolia*, retrieved on Jul. 12, 2023 at https://plants.ces.ncsu.edu/plants/magnolia-laevifolia/, 4 pp. (Year: 2023).*

* cited by examiner

*Primary Examiner* — June Hwu
(74) *Attorney, Agent, or Firm* — Weatherly IP Solutions, LLC; James M. Weatherly

(57) ABSTRACT

A new cultivar of *Magnolia* plant named 'SL01' that is characterized by its compact well-branched upright plant habit, self-cleaning fragrant cream flowers borne in profusion in spring and a high tolerance of heat and humidity.

2 Drawing Sheets

Genus and species: *Magnolia laevifolia* x *figo*.
Variety denomination: 'SL01'.

BACKGROUND OF THE NEW PLANT

The present invention relates to a new and distinct cultivar of *Magnolia* grown as an ornamental plant for use in the garden and landscape. The new cultivar is known botanically as *Magnolia laevifolia* x *figo* and will be referred to hereinafter by the cultivar name 'SL01'. This application is co-pending with the application for the inventors' variety of *Magnolia* plant named 'HYB01' (U.S. Plant patent application Ser. No. 18/184,538).

'SL01' arose from a breeding program conducted by the inventor in Kariong, New South Wales, Australia. The breeding program was commenced in 2000 with the objectives of developing varieties of *Magnolia* which are suitable for pot or container production, with compact plant habits and profuse flowering in a range of flower colors.

The male parent of 'SL01' is an unnamed *Magnolia laevifolia* (species, unpatented) and the female parent of 'SL01' is an unnamed *Magnolia figo* (species unpatented). In 2000, the inventor first emasculated flowers of *Magnolia laevifolia* and covered the emasculated flowers to exclude other pollination. The emasculated flowers were hand-pollinated by the inventor using pollen from *Magnolia figo*. The inventor collected the resultant seed from this controlled pollination and evaluated the growth and appearance of the hybrids until 2005 when the inventor selected 'SL01'.

'SL01' was first propagated by the inventor in 2005, using stem cuttings in Kariong, New South Wales, Australia. The inventor has determined that 'SL01' is stable and remains true to type in successive generations of asexual propagation.

SUMMARY

The following traits have been repeatedly observed and represent the characteristics of the new *Magnolia* cultivar 'SL01'. 'SL01' has not been tested under all possible conditions and phenotypic differences may be observed with variations in environmental, climatic and cultural conditions, however, without any variance in genotype.

1. 'SL01' exhibits a compact well-branched upright plant habit.
2. A one year old plant of 'SL01' is approximately 50 cm. in height and 20 cm. in width.
3. A seven year old plant of 'SL01', growing in a large container achieves a height of 120 cm. and a width of 95 cm.
4. 'SL01' flowers profusely in spring, bearing approximately 500 flowers at peak flowering in mid to late March.
5. The flowers of 'SL01' are cream colored when opening, then developing red-purple tinges close to and at the margins and towards the base.
6. The flowers of 'SL01' are self-cleaning and liable to shatter when touched.
7. The foliage of 'SL01' is dark olive-green in color.
8. 'SL01' grows well in moist well-drained soils in full sun to partial shade.

9. 'SL01' exhibits a high degree of tolerance of high temperatures and high humidity.
10. 'SL01' is hardy at least to USDA Zone 8.

BRIEF DESCRIPTION OF THE PHOTOGRAPHS

The accompanying color photographs illustrate the overall appearance of the new *Magnolia* variety 'SL01' showing colors as true as it is reasonably possible to obtain in colored reproductions of this type. Colors in the photographs may differ from the color values cited in the detailed botanical description, which accurately describe the actual colors of the new variety 'SL01'. The photographs were taken in Santa Barbara, California from plants in 15 gallon containers which have grown outdoors.

BOTANICAL DESCRIPTION OF THE PLANT

Figure 1:
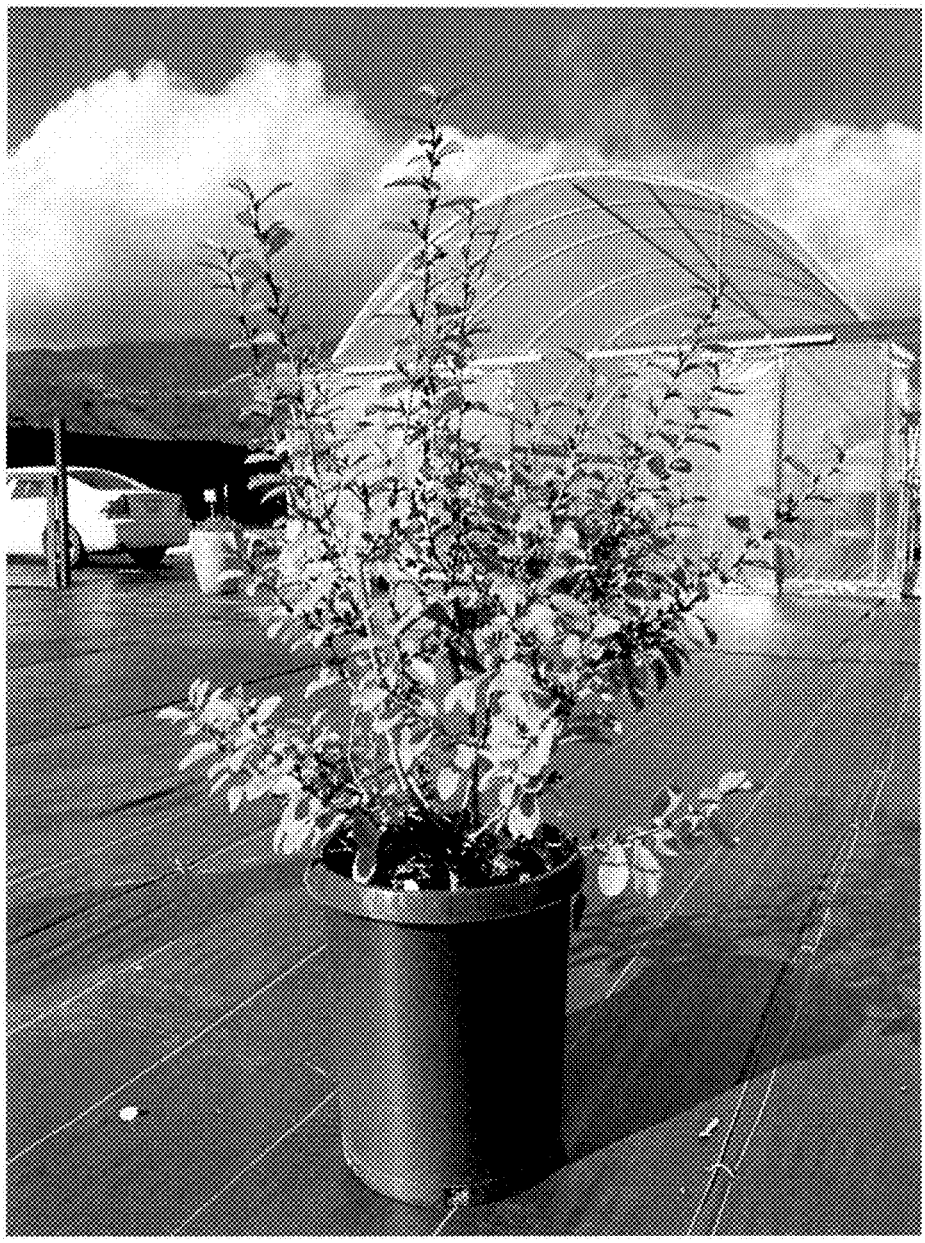
FIG. 1 depicts a four-year-old container-grown plant of 'SL01' in early spring.
Figure 2:
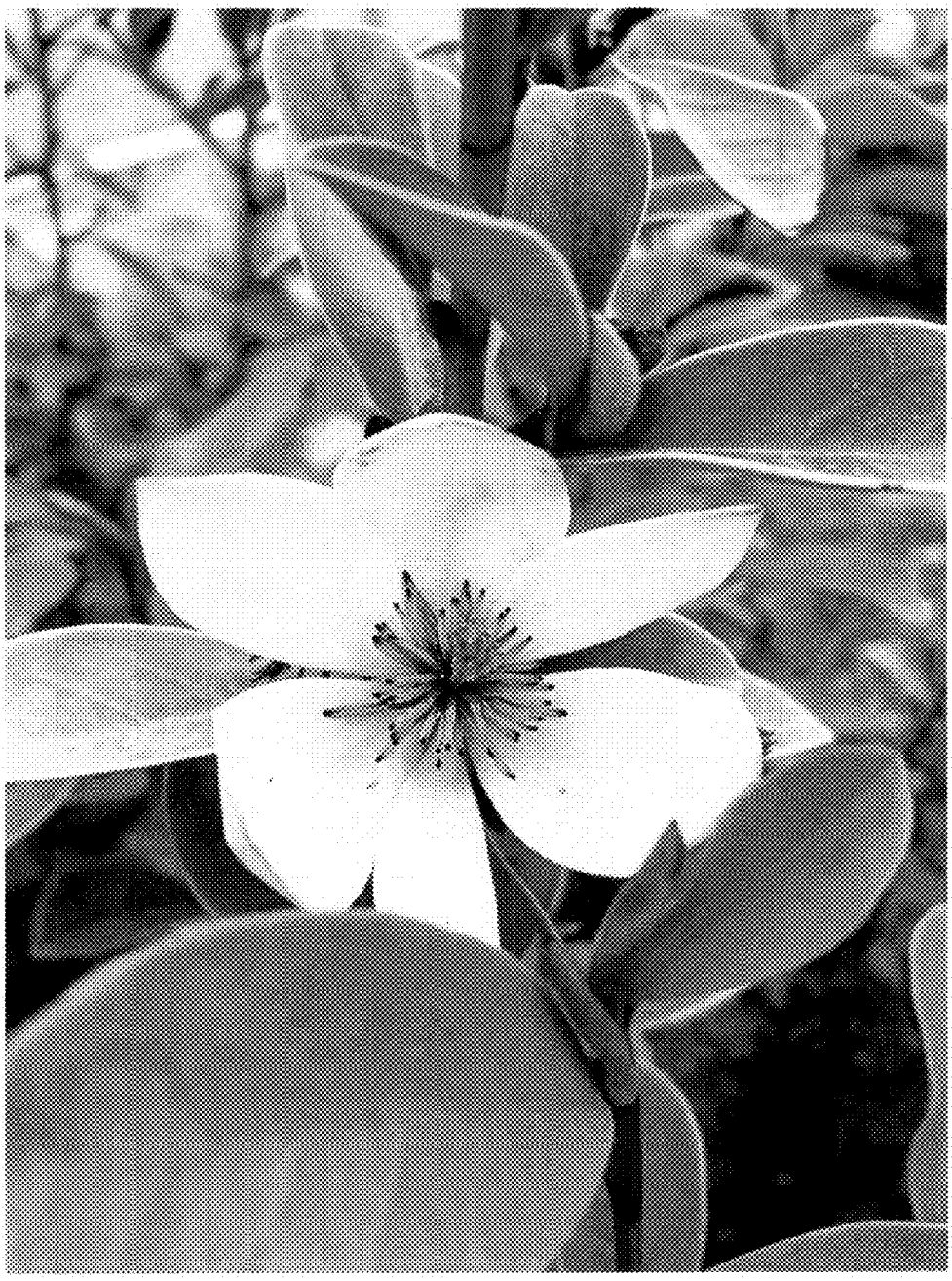
FIG. 2 depicts a close-up view of the buds and flowers of 'SL01'.

The following is a detailed description of the new cultivar 'SL01'. Data was collected from four year old plants grown outdoors in 15 gallon containers in Santa Barbara, California. The color determinations are in accordance with the 2007 edition of the Colour Chart of The Royal Horticultural Society, London, England, except where general color terms of ordinary dictionary significance are used. No chemicals were used to treat the plants. Growing conditions are typical of other *Magnolia*.

Botanical classification: *Magnolia*.
- *Variety*.—'SL01'.
- *Species*.—*Magnolia laevifolia* x *figo*.

Parentage:
- *Male parent*.—Unnamed *Magnolia laevifolia*.
- *Female parent*.—Unnamed *Magnolia figo*.

Plant description:
- *Growth habit*.—Upright, broad vase-shaped.
- *Use*.—In containers and for planting in the landscape.
- *Suitable container sizes*.—3 gallon, 5 gallon and larger containers.
- *Dimensions after four years* (*growing in a 5 gallon container*).—120 cm. in height, and 95 cm. in width.
- *Hardiness*.—At least hardy to USDA Zone 8.
- *Propagation*.—Stem cuttings.
- *Time to initiate roots*.—5 to 6 weeks are required to produce roots on an initial cutting.
- *Crop time*.—One year to 18 months are required to produce a finished one-gallon container from a rooted cutting.
- *Root system*.—Fibrous.
- *Light*.—Plant or position container in full sun or partial shade.
- *Soil*.—Plant in moist but well drained soil.
- *Type*.—Small tree, evergreen in Zone 8 and warmer.
- *Seasonal interest*.—Cream-white flowers, tinged with red-purple in early and mid-spring.

Stem (from soil level to first primary branch):
- *Shape*.—Round cross-section.
- *Dimensions*.—5 cm.-8 cm. in length, 5 cm. in diameter at soil level.
- *Color*.—198D with longitudinal striations 174A.
- *Surface*.—Lignified, rough, glabrous. Lenticels absent.

Branches:
- *Quantity*.—3 primary branches arising at or up to 8 cm. above soil level. 30-35 secondary branches and secondary branch laterals.
- *Branch dimensions: Primary branches:* 60 cm.-85 cm. in length, 5 cm. in diameter at base, 5 mm.-8 mm. in diameter towards apex. Secondary branches: 45 cm.-60 cm. in length, 2 cm. in diameter at base, 5 mm.-0 6 mm. towards apex.
- *Branch shape*.—Geniculate (zig-zag angled at each node), round cross-section.
- *Internode distance*.—12 mm.-15 mm.
- *Color*.—Older wood (2 or more years old): As stem, 198D. Newer growth (current and previous years): Ranges between 151A and 153D.
- *Surface*.—Older wood (2 or more years old): Rough, longitudinally ridged. Newer growth (current and previous years): Smooth, with dense very dark brown pubescence. Hairs fine and very short (less than 0.25 mm.), color 200A.

Foliage:
- *Leaf arrangement*.—Alternate.
- *Leaf division*.—Simple.
- *Leaf shape*.—Ovate, longitudinally concave (upper surface).
- *Leaf aspect*.—Ranges between 20 degrees to 40 degrees above the horizontal.
- *Leaf attachment*.—Short petiolate.
- *Petiole dimensions*.—4 mm.-7 mm. in length and 2 mm.-2.5 mm. in diameter.
- *Petiole color*.—Ranges between 151A and 153D.
- *Leaf dimensions*.—65 mm. in length, 33 mm. in width.
- *Leaf surface* (*adaxial*).—Smooth, glabrous, glossy.
- *Leaf surface* (*abaxial*).—Smooth, glabrous, matte.
- *Leaf color* (*adaxial*).—146A.
- *Leaf color* (*abaxial*).—146D.
- *Leaf apex*.—Rounded.
- *Leaf base*.—Broadly acute, almost rounded.
- *Leaf margin*.—Smooth, entire.
- *Leaf venation pattern*.—Pinnate.
- *Veins* (*adaxial surface*).—Veins and midrib appear as minutely raised only, color as leaf blade 146A.
- *Veins* (*abaxial surface*).—Appear as very faint depressions, color as blade, except midrib raised approximately 0.25 mm. with very lightly pubescence, color 174B, towards petiole.

Inflorescence:
- *Flower description*.—Flower type and habit: Globular to bowl shaped, held upright. Persistent or self-cleaning: Self cleaning. Quantity: one bud per node; more than 500 buds per plant in March. Natural flowering season: Commencing in late fall and peaking in early spring (mid-March to late March). Age of plants when first flowering: Most plants flower within the first year of growth from budding. Flower longevity on the plant: 7-9 days from first opening to shedding of tepals. Fragrance: Strong honeyed perfume. Shape: Globular, bowl shaped. Diameter: 30 mm.-35 mm. Depth (height): 25 mm.-30 mm. from tepal base. Flower buds (prior to showing color): Shape: Ovoid. Dimensions: 20 mm.-25 mm. in length, 11 mm.-13 mm. in diameter. Color: Green 146D beneath (when scraped) dense dark brown pubescence. Hairs: very short, less than 0.25 mm. in length, color 172A.

*Tepals.*—Number: 6. Arrangement: Overlapping. Strength: Weak: tepals fall away with light touch. Flowers will shatter in high wind. Dimensions: 30 mm. in length and 16 mm. in width. Shape: Broadly elliptic. Apex: Rounded. Base: Truncate. Margin: Entire. Surface texture: Waxy, glabrous. Color (both surfaces): Cream, ranging between 155A and 2D when opening and developing pale red-purple (59D) tinges close to and at the margins and towards the base.

*Peduncles.*—Dimensions: Approximately 15 mm in length and 6 mm in diameter. Color: As bud: green 146D beneath (when scraped) dense dark brown pubescence. Hairs very short, less than 0.25 mm in length, color ranges between 165A and 200D.

Reproductive organs:

*Stamens.*—Quantity: 45-50.

*Filaments.*—Short, 3 mm in length, 1 mm in diameter and subtending longitudinal anthers.

*Filament color.*—N77A towards base, becoming lighter N77B towards anthers.

*Anther shape.*—Awl shaped, longitudinally furrowed terminating in small conical apical tip.

*Anther dimensions.*—5 mm.-6 mm. in length, 2 mm. in width.

*Anther color.*—161B, except apical tip 79A.

*Pollen amount.*—None observed.

*Pistil quantity.*—1.

*Pistil length.*—16 mm. including pistil stem (5 mm. in length) and terminal carpel cluster (11 mm. in length).

*Pistil diameter.*—2 mm. (pistil stem) and 3 mm. (carpel cluster).

*Stigma shape.*—Round.

*Stigma color.*—143C.

*Style length.*—Approximately 5 mm.

*Style color.*—Overall 199C with darker circular scars , color 199A, where stamens have fallen away.

*Ovary.*—Observed immature and undeveloped. Shape approximately spherical, color 144C.

*Seed.*—No seed has been observed.

COMPARISON WITH PARENTS

In comparison with both parents, the growth habit of 'SL01' is shorter and more compact overall. In addition, the abaxial leaf surfaces of *Magnolia laevifolia* are pubescent whereas the abaxial leaf surfaces of 'SL01' are smooth.

COMPARISON WITH CLOSEST KNOWN VARIETY

The closest comparison variety known to the inventor is the inventor's co-pending variety, *Magnolia* Plant Named 'HYB01' which shares the same parentage. In comparison, the plant size of 'SL01' is slightly shorter in height and narrower in width. The leaves of 'SL01' are smaller and more narrow than the leaves of 'HYB01'. The tepals of 'SL01' are predominantly pale cream in color, faintly tinged with red-purple margins, whereas the tepals of 'HYB01' are pale cream in color, heavily flecked and mottled with red-purple coloration and strongly margined with red-purple coloration.

I claim:

1. A new and distinct cultivar of *Magnolia* Plant Named 'SL01' as described and illustrated herein.

* * * * *